(12) United States Patent
LeVaughn et al.

(10) Patent No.: US 11,395,837 B2
(45) Date of Patent: Jul. 26, 2022

(54) PLACENTAL TISSUE COMPONENT COMPOSITIONS FOR TREATMENT OF SKIN DEFECTS AND METHODS USING SAME

(71) Applicant: MiMedx Group, Inc., Marietta, GA (US)

(72) Inventors: Rick LeVaughn, Marietta, GA (US); Sivakkumar Arjunon, Marietta, GA (US); Olivia Taylor, Marietta, GA (US)

(73) Assignee: MiMedx Group, Inc., Marietta, GA (US)

( * ) Notice: Subject to any disclaimer, the term of this patent is extended or adjusted under 35 U.S.C. 154(b) by 0 days.

(21) Appl. No.: 17/106,916

(22) Filed: Nov. 30, 2020

(65) Prior Publication Data
US 2021/0093675 A1 Apr. 1, 2021

Related U.S. Application Data (63) Continuation of application No. 16/416,875, filed on May 20, 2019, now Pat. No. 10,849,933.

(60) Provisional application No. 62/673,528, filed on May 18, 2018.

(51) Int. Cl.
| | |
|---|---|
| *A61K 35/50* | (2015.01) |
| *A61K 35/51* | (2015.01) |
| *A61K 9/00* | (2006.01) |
| *A61L 27/36* | (2006.01) |
| *A61K 9/14* | (2006.01) |
| *A61L 27/38* | (2006.01) |
| *A61K 9/19* | (2006.01) |

(52) U.S. Cl.
CPC ............ *A61K 35/50* (2013.01); *A61K 9/0019* (2013.01); *A61K 9/146* (2013.01); *A61K 9/19* (2013.01); *A61K 35/51* (2013.01); *A61L 27/3683* (2013.01); *A61L 27/3804* (2013.01)

(58) Field of Classification Search
CPC ................................ A61K 9/10; A61K 9/0019
See application file for complete search history.

(56) References Cited

U.S. PATENT DOCUMENTS

| | | | |
|---|---|---|---|
| 8,071,135 B2 | 12/2011 | Liu et al. | |
| 2002/0160510 A1 | 10/2002 | Hariri | |
| 2014/0017280 A1* | 1/2014 | Daniel | .................... A61P 29/00 424/400 |
| 2015/0064274 A1 | 3/2015 | Koob | |
| 2016/0263281 A1 | 9/2016 | Koob et al. | |

FOREIGN PATENT DOCUMENTS

WO  WO 2013/082158 A1  6/2013

OTHER PUBLICATIONS

AEDICELL/: "Dermavest," https://www.slideshare.net/BryanKentnerDPM/dermavest-overview [retrieved on Jun. 15, 2021], 16 pgs., Oct. 13, 2017.
European Application No. 19803338.3, Extended European Search Report dated Nov. 23, 2021.
Lemperle et al., "A Classification of Facial Wrinkles," Plast Reconstr Surg, 108(6):1735-1750, (2001).
WIPO Application No. PCT/IB2019/054157, PCT International Search Report and Written Opinion of the International Searching Authority dated Oct. 16, 2019.

* cited by examiner

*Primary Examiner* — Qiuwen Mi
(74) *Attorney, Agent, or Firm* — Alston & Bird LLP (57) ABSTRACT

The present disclosure provides methods of treating defects such as wrinkles or scars via a subdermal injection of placental tissue components. It also provides placental tissue compositions maintained within the barrel of a syringe, which may be for use in treating such defects.

11 Claims, 4 Drawing Sheets

PLACENTAL TISSUE COMPONENT COMPOSITIONS FOR TREATMENT OF SKIN DEFECTS AND METHODS USING SAME

RELATED APPLICATIONS

This application is a continuation of U.S. application Ser. No. 15/895,546, filed Feb. 13, 2018, which claims the benefit of U.S. Provisional App. No. 62/673,528 filed May 18, 2018, which are incorporated by reference herein in their entirety.

FIELD OF THE INVENTION

This disclosure relates generally to a method of treating age-related skin conditions such as wrinkles by injecting a combination of placental tissues, such as amnion, chorion, umbilical cord and/or placental disc.

BACKGROUND

Wrinkles and other unsightly skin conditions are often the result of dermatological breakdown such as loss of collagen and other connective tissues. While such breakdown can be generically referred to as wrinkles or scars (such as acne scars), their development is indicative of an underlying condition. The resulting wrinkles and/or scars are often accompanied by emotional and/or psychological concerns by the patient.

Forbes has estimated that the personal appearance industry was responsible for $445 billion in sales last year. This large volume of sales is strong evidence of the high demand for products that can help improve a patient's outward appearance, particularly in the facial area.

One particular area where personal appearance products have been selling especially well is in the area of wrinkles and scarring therapies. Products in this area are generally targeted toward reducing the natural effects of dermatological breakdown. With respect to the face, dermatological breakdown typically results in loss of muscle tone and thinning skin which may give the face a flabby or droopy appearance. The skin also begins to dry out with age, and lose fat, which results in the loss of a plump, smooth surface. Extended exposure to environmental factors such as smoking and sunlight tends to increase and enhance the appearance of wrinkles. Wrinkles tend to become most prominent around the corners of the eyes and the naso-labial folds. Blotches and dark spots may become more apparent as well.

A number of different products have been developed in order to combat the appearance of wrinkles and scars. Some of these products can be applied directly to the skin, while others are injected directly into the wrinkle or scar site. Botox is a toxin derived from bacteria that can be used to temporarily paralyze certain facial muscles so that they will not pull on the skin and increase the appearance of wrinkles. Other injectable products function as fillers that are administered via a subdermal injection at the site of the wrinkle or scar where they fill in the subdermal void space, reducing the appearance of the wrinkle or scar. The market for dermal fillers in North America and Europe is expected to reach sales of $2.8 billion by 2026. Some common wrinkle filler products include hyaluronic acid, collagen, silicone, and autologous fat. While these injectable fillers are effective to varying degrees, they can all result in the patient experiencing side effects, such as allergic reactions, swelling, bruising, disfigurement, nerve paralysis, and skin discoloration.

Additionally, many of these injectable fillers are eventually resorbed by the body at varying rates and require multiple follow up injections in order to maintain the patient's original results. Still further, the use of an injectable composition is problematic as most patients suffer from injection site inflammation, swelling, redness, and discomfort that can last up to several days.

Accordingly, there is a need for a product that reduces wrinkles and scars as well as inhibits inflammation at the injection site.

SUMMARY OF THE INVENTION

This invention is directed to an injectable composition that treats wrinkles, scarring and other deformities while also providing for anti-inflammatory properties that address the inflammation, swelling and redness that accompanies the injection(s).

In one embodiment, this invention provides for a rehydrated composition comprising at least one placental tissue component. In an embodiment, the composition comprises placental and/or umbilical cord components selected from the group consisting of placental disc, amnion tissue, chorion tissue, and umbilical cord tissue. In a further embodiment, the placental and/or umbilical cord components have a size of no greater than 150 microns. In an embodiment, said composition, when reconstituted with an aqueous solution, provides for a paste that is pseudo thixotropic in nature such that the composition has a flow rate at room temperature through a 27 gauge needle of from about 0.05 mL/sec to 0.75 mL/sec.

Human placental membrane (e.g. amniotic membrane or tissue) has been used for various types of reconstructive surgical procedures since the early 1900s. The membrane serves as a substrate material, more commonly referred to as a biological dressing or patch graft. Such a membrane has also been used widely for ophthalmic procedures. Typically, such membrane is either frozen or dried for preservation and storage until needed for surgery.

Such placental tissue is typically harvested after an elective Cesarean surgery. The placenta is composed of the umbilical cord and amniotic sac. The amniotic sac, commonly referred to as the amniotic membrane, has two primary layers of tissue, amnion and chorion. Amnion tissue is innermost layer of the amniotic sac and in direct contact with the amniotic fluid. The amniotic sac contains the amniotic fluid and protects the fetal environment. Histological evaluation indicates that the membrane layers of the amnion consist of single layer of epithelium cells, thin reticular fibers (basement membrane), a thick compact layer, and fibroblast layer. The fibrous layer of amnion (i.e., the basement membrane) contains collagen types IV, V, and VII, and cell-adhesion bio-active factors including fibronectin and laminins.

After harvesting, the placental tissue is separated out into three distinct components: the umbilical cord, the amniotic/chorionic membrane and the placental disc. All components are sourced from a single donor. Each of the three components is subject to a specific process in which the individual component is rinsed in an antibiotic solution, and then rinsed again to remove any residual antibiotic.

Preferably, the placental tissue component is cleaned in a hyperisotonic solution wherein the hyperisotonic solution comprises NaCl concentration in a range of from about 30% to about 10%.

In some embodiments, the method further includes the step of, after separation of the chorion tissue layer from the amniotic membrane layer, physically cleaning the selected layer to remove blood clots and other contaminants. Specifically, the spongy intermediate layer that is found between the amnion and chorion layers in naturally occurring placental tissue is removed from these layers during processing and, in some embodiments, discarded.

With respect to the umbilical cord, the vein and arteries are removed and the remaining umbilical tissue is gently cleansed and minimally manipulated to preserve inherent growth factors and proteins in the tissue. Notable growth factors in the umbilical cord include transforming growth factor beta (TGF-β), basic fibroblast growth factor (bFGF), platelet derived growth factors (PDGF AA & BB), and vascular endothelial growth factor (VEGF)14,15, which are known to regulate wound healing.

The amniotic and chorionic membranes are gently cleansed and minimally manipulated to preserve inherent growth factors (over 200+) and proteins in the tissue. Notable growth factors in the amniotic and chorionic membranes include epidermal growth factor (EGF), transforming growth factors alpha and beta (TGF-α & β), basic fibroblast growth factor (bFGF), platelet derived growth factors (PDGF AA & BB), and vascular endothelial growth factor (VEGF)14,15.

The placental disc tissue is subjected to the same cleansing process as the membranes and umbilical tissue and are also subjected to an additional decellularization step. The decellularization process aims to rid the placental tissue of antigenic agents by substantially reducing the presence of maternal DNA. Decellularization also reduces the presence of growth factors and other soluble or intracellular proteins while retaining the basic extracellular matrix components.

Once the respective components that are to be used have been decontaminated and rinsed (and, in the case of the placental disc tissue, decellularized) the components are recombined and dehydrated via lyophilization. After the tissues have been dehydrated, the tissues are then milled to the appropriate size to allow the processed tissue to be injected at a wrinkle site.

The finished product is packaged in a sterile container and is reconstituted with an acceptable excipient by the end user.

In some embodiments, the particle size is modified in order to affect the viscosity and stability of the resulting injectable product.

In some embodiments, the relative ratios of the placental disc tissue, amniotic/chorionic membrane and umbilical tissue are adjusted to affect the viscosity and stability of the resulting injectable product In some aspects, this disclosure provides methods of treatment for administering a placental tissue-based injectable to reduce the appearance of wrinkles in a patient.

In some aspects, this disclosure provides an apparatus for administering a placental tissue-based injectable to reduce the appearance of wrinkles in a patient.

BRIEF DESCRIPTION OF THE FIGURES

FIG. 1A illustrates two syringes, a luer connector, and a micro-vial. FIG. 1B shows the assembled apparatus.

DETAILED DESCRIPTION OF THE INVENTION

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs. Although any methods and materials similar or equivalent to those described herein can also be used in the manufacture, practice or testing of the present invention, the preferred methods and materials are now described. All patents and publications mentioned herein are incorporated by reference to disclose and describe the methods and/or materials in connection with which the publications are cited.

Each embodiment disclosed herein is contemplated as being applicable to each of the other disclosed embodiments. All combinations and sub-combinations of the various elements described herein are within the scope of the embodiments.

It is understood that where a parameter range is provided, all integers and ranges within that range, and tenths and hundredths thereof, are also provided by the embodiments. For example, "5-10%" includes 5%, 6%, 7%, 8%, 9%, and 10%; 5.0%, 5.1%, 5.2% . . . 9.8%, 9.9%, and 10.0%; and 5.00%, 5.01%, 5.02% . . . 9.98%, 9.99%, and 10.00%, as well as, for example, 6-9%, 5.1%-9.9%, and 5.01%-9.99%.

As used herein, "about" in the context of a numerical value or range means within ±1%, ±5%, or 10% of the numerical value or range recited or claimed.

The invention illustratively disclosed herein suitably may be practiced in the absence of any element which is not specifically disclosed herein.

It must be noted that as used herein and in the appended claims, the singular forms "a", "an", and "the" include plural referents unless the context clearly dictates otherwise. Thus, for example, reference to "a pluripotent stem cell" includes a plurality of pluripotent stem cells.

Definitions

As used herein the following terms have the following meanings.

"Comprising" or "comprises" is intended to mean that the compositions, for example media, and methods include the recited elements, but not excluding others. "Consisting essentially of" when used to define methods, shall mean excluding other elements of any essential significance to the combination for the stated purpose. "Consisting of" shall mean excluding substantial method steps. Embodiments defined by each of these transition terms are within the scope of this invention.

"Optional" or "optionally" means that the subsequently described event or circumstance can or cannot occur, and that the description includes instances where the event or circumstance occurs and instances where it does not.

"Rehydrated" refers to a composition, particle, or other substance which was previously, but is no longer, dehydrated. Rehydration may be accomplished by putting the dehydrated substance in an aqueous solution (such as a 0.9% saline solution) or by other means known in the art.

The term "subject" as used herein is any vertebrate organism including but not limited to mammalian subjects such as humans, farm animals, domesticated pets and the like. The term "patient" may be used interchangeably with "subject."

The term "placental tissue" refers to any and all of the well-known components of the placenta including but not limited to amnion, chorion, intermediate layer, Wharton's Jelly, placental disc, umbilical cord and the like.

The term "treat," with respect to a defect, means to reduce the severity of the defect, or to eliminate it entirely.

The term "defect" refers to any undesirable aesthetic characteristic including, but not limited to wrinkles, furrows, folds, lines or scars which may be present in the patient especially in the facial area of the patient. A more detailed discussion of such defects, wrinkle types and wrinkle severity may be found at "A Classification of Facial Wrinkles" Gottried, et al; Cosmetic; 2001, the contents of which are incorporated herein by reference.

Methods of Manufacture
Initial Tissue Collection

The recovery of placenta tissue originates in a hospital, where it is collected during a Cesarean section birth. The donor, referring to the mother who is about to give birth, voluntarily submits to a comprehensive screening process designed to provide the safest tissue possible for transplantation. The screening process preferably tests for antibodies to the human immunodeficiency virus type 1 and type 2 (anti-HIV-1 and anti-HIV-2), hepatitis B surface antigens (HBsAg), antibodies to the hepatitis C virus (anti-HCV), antibodies to the human T-lymphotropic virus type I and type H (anti-HTLV-I and anti-HTLV-II), CMV, and syphilis, using conventional serological tests. The above list of tests is exemplary only, as more, fewer, or different tests may be desired or necessary over time or based upon the intended use of the grafts, as will be appreciated by those skilled in the art.

Based upon a review of the donor's information and screening test results, the donor will either be deemed acceptable or not. In addition, at the time of delivery, cultures are taken to determine the presence of, for example, *Clostridium* or *Streptococcus*. If the donor's information, screening tests, and the delivery cultures are all negative (i.e., do not indicate any risks or indicate acceptable level of risk), the donor is approved and the tissue specimen is designated as initially eligible for further processing and evaluation.

Human placentas that meet the above selection criteria are preferably individually bagged in a saline solution in a sterile shipment bag and stored in a container of wet ice for shipment to a processing location or laboratory for further processing.

Material Check-In and Evaluation

Upon arrival at the processing center or laboratory, the shipment is opened and verified that the sterile shipment bag/container is still sealed and intact, that ice or other coolant is present and that the contents are cool, that the appropriate donor paperwork is present, and that the donor number on the paperwork matches the number on the sterile shipment bag containing the tissue. The sterile shipment bag containing the tissue is then stored in a refrigerator until ready for further processing. All appropriate forms are completed and chain of custody and handling logs are also completed.

Gross Tissue Processing Step

When the tissue is ready to be processed further, the sterile supplies necessary for processing the placenta tissue further are assembled in a staging area in a controlled environment and are prepared for introduction into a critical environment. If the critical environment is a manufacturing hood, the sterile supplies are opened and placed into the hood using conventional sterile technique. If the critical environment is a clean room, the sterile supplies are opened and placed on a cart covered by a sterile drape. All the work surfaces are covered by a piece of sterile drape using conventional sterile techniques, and the sterile supplies and the processing equipment are placed on to the sterile drape, again using conventional sterile technique.

If the placenta tissue is collected prior to the completion or obtaining of results from the screening tests and delivery cultures, such tissue is labeled and kept in quarantine. The tissue is approved for further processing only after the required screening assessments and delivery cultures, which declare the tissue safe for handling and use, are satisfied.

Processing equipment is decontaminated according to conventional and industry-approved decontamination procedures and then introduced into the critical environment. The equipment is strategically placed within the critical environment to minimize the chance for the equipment to come in proximity to or be inadvertently contaminated by the tissue specimen.

Next, the placenta is removed from the sterile shipment bag and transferred aseptically to a sterile processing basin within the critical environment. The sterile basin contains, preferably, 18% NaCl (hyperisotonic saline) solution that is at room or near room temperature. The placenta is gently massaged to help separate blood clots and to allow the placenta tissue to reach room temperature, which will make the separation of the amnion and chorion layers from each other, as discussed hereinafter, easier. After having warmed up to the ambient temperature (after about 10-30 minutes), the placenta is then removed from the sterile processing basin and laid flat on a processing tray with the amniotic membrane layer facing down for inspection.

Next, if the placenta tissue is deemed acceptable for further processing, the amnion and chorion layers of the placenta tissue are then carefully separated. The materials and equipment used in this procedure include the processing tray, 18% saline solution, sterile 4×4 sponges, and two sterile Nalgene jars. The placenta tissue is then closely examined to find an area (typically a corner) in which the amniotic membrane layer can be separated from the chorion layer. The amniotic membrane appears as a thin, opaque layer on the chorion.

With the placenta tissue in the processing tray with the amniotic membrane layer facing down, the chorion layer is gently lifted off the amniotic membrane layer in a slow, continuous motion, using care to prevent tearing of the amniotic membrane. If a tear starts, it is generally advisable to restart the separation process from a different location to minimize tearing of either layer of tissue. The separation process continues by hand, without the use of the sponges, being careful not to tear either the amnion layer or the chorion layer.

Care is then taken to remove blood clots and other extraneous tissue from each layer of tissue until the amniotic membrane tissue and the chorion are clean and ready for further processing. More specifically, the amnion and chorion tissues are placed on the processing tray and blood clots are carefully removed using a blunt instrument, a finger, or a sterile non-particulating gauze, by gently rubbing the blood until it is free from the stromal tissue of the amnion and from the trophoblast tissue of the chorion. The stromal layer of the amnion is the side of the amniotic membrane that faces the mother. In contrast, the basement membrane layer is the side of the amnion that faces the fetus.

Using a blunt instrument, a cell scraper or sterile gauze, any residual debris or contamination is also removed. This step must be done with adequate care, again, so as not to tear the amnion or chorion tissues. The cleaning of the amnion is complete once the amnion tissue is smooth and opaque-white in appearance. If the amnion tissue is cleaned too much, the opaque layer can be removed. Any areas of the amnion cleaned too aggressively and appear clear will be unacceptable and will ultimately be discarded.

After the amnion and chorion have been separated from the placenta, the remaining components of the placenta are also processed. Specifically, the umbilical cord is removed from the placenta. The umbilical cord is cut open and the umbilical vein and arteries (which contain maternal DNA and antigens) are then removed. The remaining tissue is retained, which comprises the umbilical cord and Wharton's jelly. After the umbilical cord and amnion/chorion have been removed from the placenta, the remaining placental disc tissue is also retained and set aside for additional processing. All of the retained tissue components are subject to a chemical decontamination step.

Chemical Decontamination Step

The retained placental tissue components (amnion/chorion, placental disc, and umbilical cord) are then placed into a sterile Nalgene jar for the next step of chemical decontamination. Any undesired placental tissue components are discarded in an appropriate biohazard container.

Next, each Nalgene jar is aseptically filled with 18% saline solution and sealed (or closed with a top). The jar is then placed on a rocker platform and agitated for between 30 and 90 minutes, which further cleans the tissue of contaminants.

If the rocker platform was not in the critical environment (e.g., the manufacturing hood), the Nalgene jar is returned to the critical/sterile environment and opened. Using sterile forceps, the placental tissue components are gently removed from the Nalgene jar containing the 18% hyperisotonic saline solution and placed into an empty Nalgene jar. This empty Nalgene jar with the tissue is then aseptically filled with a pre-mixed antibiotic solution. Preferably, the pre-mixed antibiotic solution is comprised of a cocktail of antibiotics, such as Streptomycin Sulfate and Gentamicin Sulfate. Other antibiotics, such as Polymixin B Sulfate and Bacitracin, or similar antibiotics now available or available in the future, are also suitable. Additionally, it is preferred that the antibiotic solution be at room temperature when added so that it does not change the temperature of or otherwise damage the tissue. This jar or container containing the tissue and antibiotics is then sealed or closed and placed on a rocker platform and agitated for, preferably, between 60 and 90 minutes. Such rocking or agitation of the tissue within the antibiotic solution further cleans the placental tissue components of contaminants and bacteria.

Again, if the rocker platform was not in the critical environment (e.g., the manufacturing hood), the jar or container containing the tissue and antibiotics is then returned to the critical/sterile environment and opened. Using sterile forceps, the placental tissue component is gently removed from the jar or container and placed in a sterile basin containing sterile water or normal saline (0.9% saline solution). The placental tissue component is allowed to soak in place in the sterile water/normal saline solution for at least 10 to 15 minutes. The placental tissue component may be slightly agitated to facilitate removal of the antibiotic solution and any other contaminants from the placental tissue component. After at least 10 to 15 minutes, the tissue is ready to be dehydrated and processed further.

Decellularization of Placental Disc Component

After the chemical decontamination step, the placental disc portion of the placental tissue components should preferably be decellularized, due to the presence of maternal antigens in this tissue which may result in an undesired immune reaction from an end user patient. Any decellularizing process known to one skilled in the art may be used, e.g., decellularization methods disclosed in U.S. Application Publication No. 2002/0160510 or U.S. Pat. No. 8,071,135. Decellularization can also be carried out via methods such as temperature methods, electrical disruption, chemical decellularization, or enzymatic decellularization. Preferably, the process used for decellularizing the placental disc tissue does not disrupt the native conformation of the proteins making up the placental disc tissue.

Dehydration/Lyophilization Step

After all components have been appropriately decontaminated and decellularized (as necessary for the placental disc component), the components are recombined and subject to a dehydration step.

Preferably, the separate placental components are placed in individual, sealed Tyvek pouches (or other commercially available pouch) and placed into a commercially available freeze drying chamber. Any lyophilization process known to one skilled in the art may be used, so long as the placental components are substantially dehydrated when the lyophilization process has been completed.

Other methods may be used to adequately dehydrate the components. Such techniques may include, but are not limited to chemical dehydration, or placing the components in a low humidity/high temperature environment for an adequate period of time until optimal dehydration of the components has been achieved. Such dehydration techniques are generally well-known to those having skill in the art.

Recombination and Milling Step

Once the placental components have been completely dehydrated, the placental components are recombined and then milled into smaller particles. In one embodiment, the ratio of recombined placental components are selected to provide a paste that has a flow rate as described above. It is understood that the particular ratios of these components are less important than the resulting flow rate such that the composition is readily injectable but also remains stationary once injected. The recombined placental components are fed into a commercially available milling apparatus. The placental components are then milled at a speed of approximately 8,000 rpm into a sieve size ranging between 50-150 μm. It is understood that the term "tissue" is the same as the term "component" as used herein.

This milling step will optimally result in a placental component particle size ranges between 70-150 μm.

In a preferred embodiment, the recombined placental tissue components should be composed of about 50-98% placental disc tissue, about 1-30% umbilical cord tissue if present, and about 1-20% amnion/chorion tissue by weight if present. In an embodiment, the recombined placental tissue components should be composed of about 60-95%, about 65-90%, about 70-85%, or about 75-80% placental disc tissue by weight. In an embodiment, the recombined placental tissue components should be composed of about 1-25%, about 5-20%, or about 10-15% umbilical cord tissue by weight. In an embodiment, the recombined placental tissue components should be composed of about 1-15%, about 4-12%, or about 8-10% amnion/chorion tissue by weight. In an embodiment, the recombined placental tissue components should be composed of about 1-15%, about 4-12%, or about 8-10% amnion tissue by weight. In an embodiment, the recombined placental tissue components should be composed of about 1-15%, about 4-12%, or about 8-10% chorion tissue by weight.

When all of the placental disc, amnion, chorion, and umbilical cord from a single donor are obtained, recombined, and dehydrated, the resulting recombined placental tissue components comprise about 11-30% non-placental disc components (i.e. amnion, chorion, and/or umbilical cord) by weight.

In an embodiment, the recombined placental tissue components comprise about 11-30% non-placental disc components by weight. In an embodiment, the recombined placental tissue components comprise about 15-25% or about 18-22% non-placental disc components by weight.

In an embodiment, the weight percentages are determined pre-dehydration. In another embodiment, the weight percentages are determined post-dehydration.

In an embodiment, the recombined placental tissue components comprise placental disc and amnion tissue. In an embodiment, the recombined placental tissue components comprise placental disc and chorion tissue. In an embodiment, the recombined placental tissue components comprise placental disc, amnion tissue, and chorion tissue.

In an embodiment, the recombined placental tissue components comprise placental disc and umbilical cord tissue.

Sifting Step

The milled particles are then subjected to a sifting step. The milled particles are placed on a commercially available sifter and placed over a sieve. The sieve size ranges from 50-150 µm. The sifter is turned on and the particles are sifted for a time period from five to twenty minutes. The sifting process results in a powder of particles that are of a uniform size of between 50-150 µm. Once the desired particle size has been achieved, the powder is then aseptically transferred into vials that can hold between 75-600 mg doses and sealed.

In an alternative embodiment, the particles may be from 50-500 µm, from 100-400 µm, from 150-300 µm, or from 200-250 µm. In an alternative embodiment, the particles may be ≤50 µm, ≤100 µm, ≤150 µm, ≤200 µm, ≤250 µm, ≤300 µm, ≤350 µm, ≤400 µm, ≤450 µm, and ≤500 µm. In an alternative embodiment, the particles may be ≥50 µm, ≥100 µm, ≥150 µm, ≥200 µm, ≥250 µm, ≥300 µm, ≥350 µm, ≥400 µm, or ≥450 µm. In an embodiment, the particles may have a range of sizes.

Reconstitution

In order to administer the particulate placental components to a subject, the end user must first reconstitute the powder by rehydrating it. Optimally, the rehydrating agent is 0.9% saline solution, but any suitable excipient may be used.

The powder is combined with the 0.9% saline solution at a ratio of between 100-150 mg of powder per 1 cc of 0.9% saline solution. In one embodiment, the desired volume of 0.9% saline solution is first transferred to an 18 gauge needle syringe. Once the 0.9% saline solution has been transferred, the needle tip is removed. The desired amount of dehydrated powder is then transferred from its vial to a second syringe. The two syringes are attached to each other by a female-to-female luer connector.

Figure 1A:
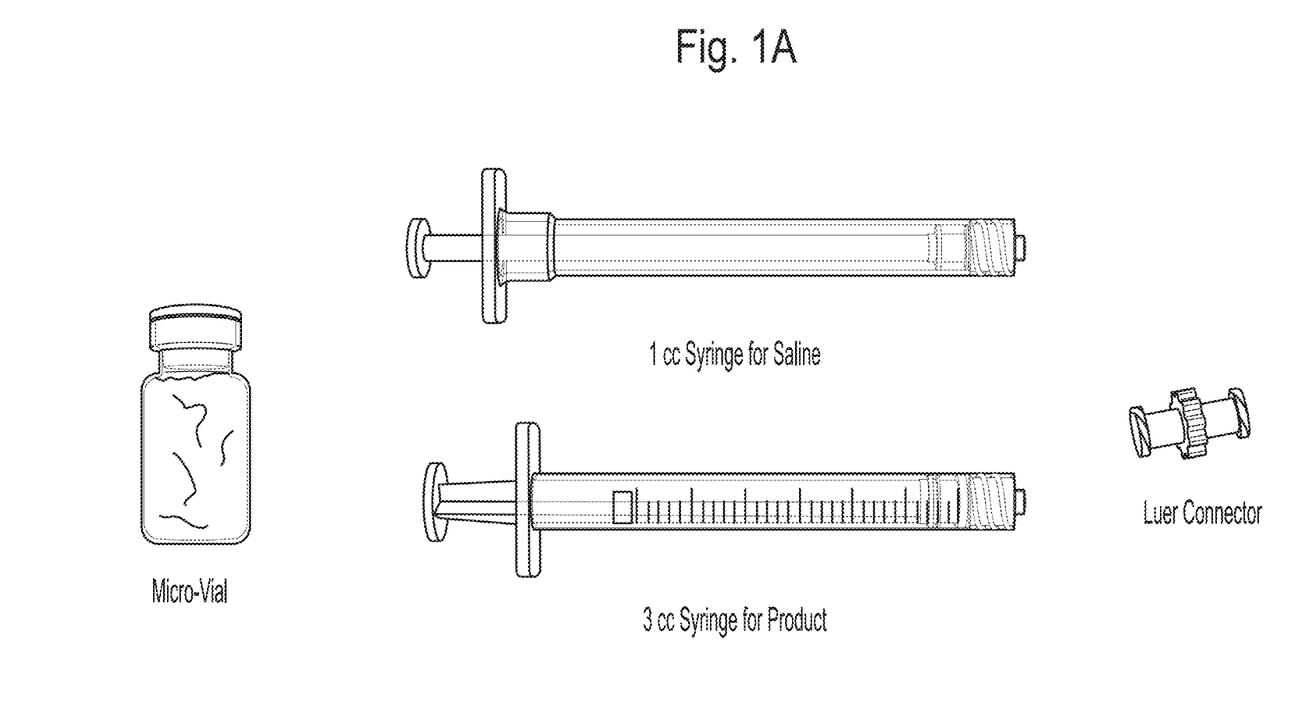
FIGS. 1A and 1B show one embodiment of the reconstitution apparatus that may be used to mix an acceptable excipient with the dried placental tissue-based injectable prior to injection.
Figure 1B:
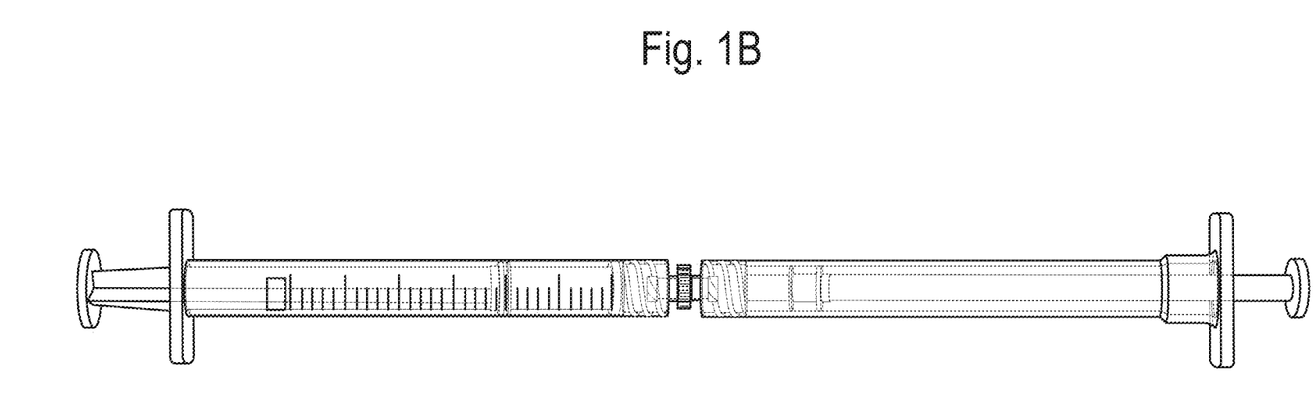

Once the syringes have been connected, the saline solution and the dehydrated powder are mixed by alternately pressing the plungers on each syringe. Complete reconstitution should take ten mixing strokes (where a stroke is defined as one complete compression of the saline plunger followed by one complete compression of the powder plunger). The individual components of this reconstitution apparatus embodiment are shown in FIG. 1A, and the assembled reconstitution apparatus embodiment is illustrated in FIG. 1B.

Once the powder has been adequately rehydrated, the connector between the two syringes is removed, and the empty syringe is discarded. A 27 gauge needle is then attached to the syringe containing the reconstituted powder.

In an embodiment, the composition further comprises hyaluronic acid.

Administration of Placental Components to a Subject

Figure 2A:
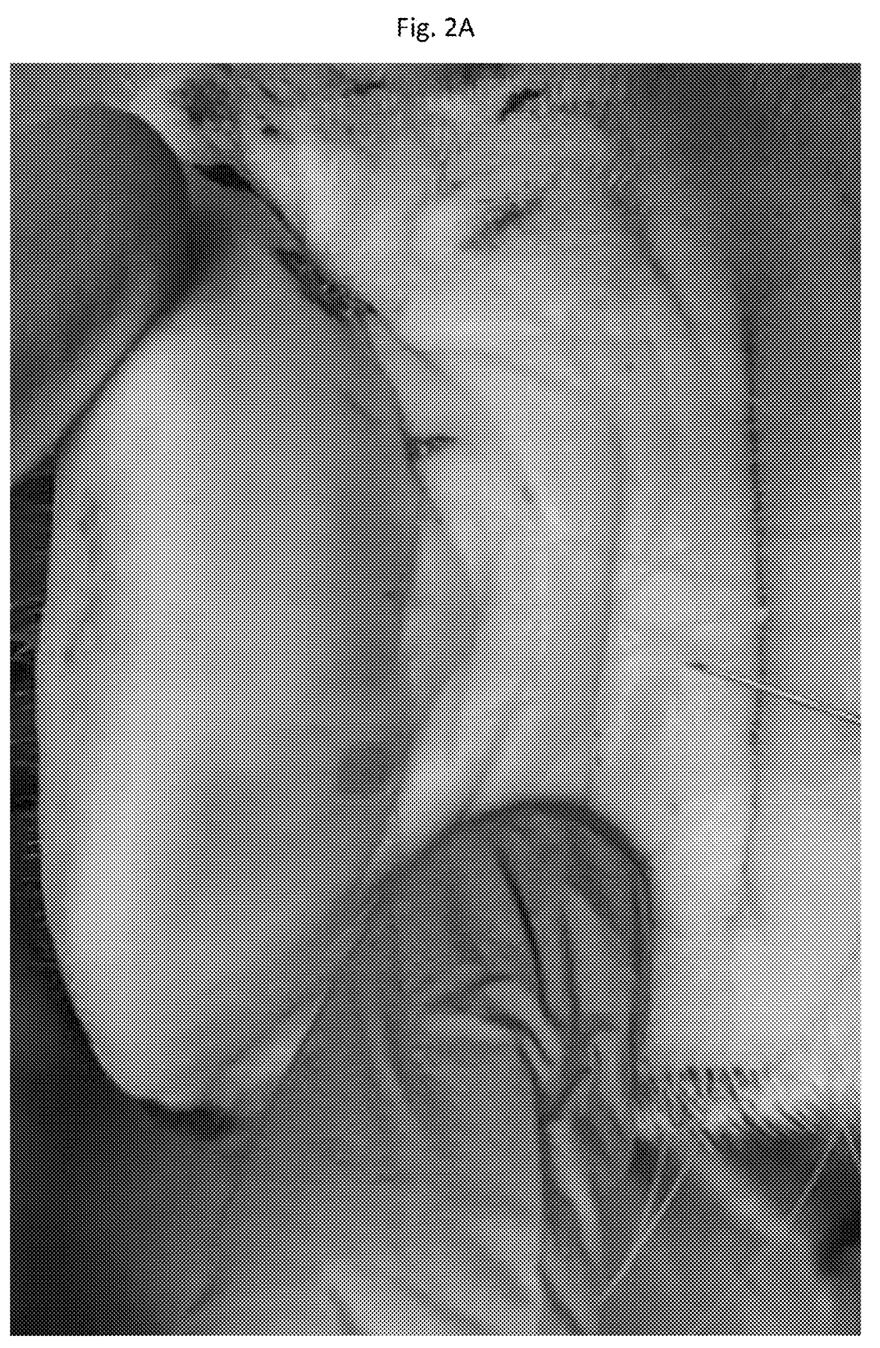
FIGS. 2A and 2B are photographs of a pig cadaver illustrating the appearance of a wrinkle before (FIG. 2A) and after (FIG. 2B) the placental tissue-based injectable has been administered.
Figure 2B:
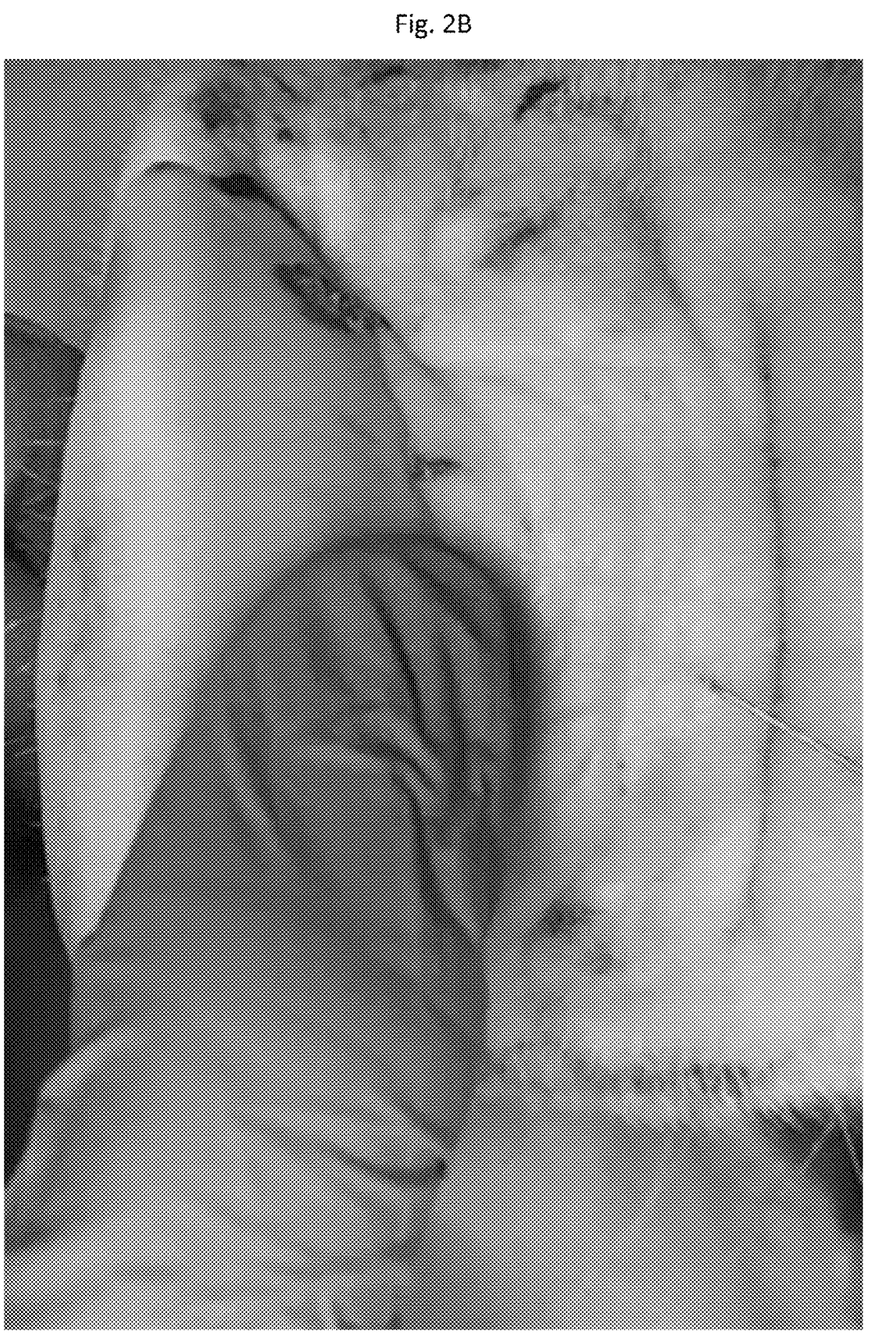

Once the powder has been rehydrated and the 27 gauge needle has been attached, the placental components can then be administered to a subject. Depending on the size and severity of the wrinkle site, 75-600 mg doses can be administered. After the dose has been administered, the subject's wrinkle should have a filled in appearance. FIGS. 2A and 2B illustrate the appearance of a wrinkle on a pig cadaver before and after, respectively, a dose comprised of 100 mg of powder in 1 mL of 0.9% saline solution has been administered. Depending upon results, the patient should return between six to nine months after administration for follow up injections.

In an embodiment, the placental components are administered in combination with a traditional product for treating defects, such as hyaluronic acid, collagen, silicone, and autologous fat. The placental components may be administered simultaneously with the traditional product (i.e. in a single composition) or contemporaneously (i.e. separately, but at the same time or sufficiently close together so as to produce an additive or synergistic effect). In an embodiment, the co-administration of the present injectable composition and the traditional product results in a synergistic effect.

What is claimed is:

1. A method of preparing an injectable placental tissue composition, said method comprising:
    a) decellularizing placental disk;
    b) dehydrating the placental disk;
    c) dehydrating one or more of amniotic membrane, chorionic membrane, and umbilical cord;
    d) combining the dehydrated placental disk with the one or more of dehydrated amniotic membrane, chorionic membrane, and umbilical cord; and
    e) milling the composition formed in step d) so as to form dehydrated particles.

2. The method of claim 1, further comprising sifting the dehydrated particles using a sieve having a size from 50-500 µm.

3. The method of claim 2, further comprising rehydrating the sifted, dehydrated particles so as to form a rehydrated composition.

4. The method of claim 3, further comprising placing the rehydrated composition in a syringe.

5. The method of claim 1, wherein the dehydrated particles are about 1-20% dehydrated amniotic membrane and/or chorionic membrane particles, if present, about 1-30% dehydrated umbilical cord particles, if present, and about 50-98% dehydrated, decellularized placental disc particles, by weight.

6. The method of claim 1, wherein the particles comprise placental disc and amniotic membrane.

7. The method of claim 1, wherein the particles comprise placental disc and chorionic membrane.

8. The method of claim 1, wherein the particles comprise placental disc, amniotic membrane, and chorionic membrane.

9. The method of claim 1, wherein the particles comprise placental disc and umbilical cord.

10. The method of claim 1, wherein the particles comprise placental disc, amniotic membrane, chorionic membrane, and umbilical cord.

11. The method of claim 1, wherein the particles have a size from about 50-150 μm.

* * * * *